(12) United States Patent
Tanaka et al.

(10) Patent No.: US 10,191,537 B2
(45) Date of Patent: Jan. 29, 2019

(54) SMART WEARABLE DEVICES AND METHODS FOR CUSTOMIZED HAPTIC FEEDBACK

(71) Applicants: SONY CORPORATION, Tokyo (JP); SONY CORPORATION OF AMERICA, New York, NY (US)

(72) Inventors: Nobuo Tanaka, Glen Rock, NJ (US); Vladimir Elgort, Staten Island, NY (US); Jacelyn Danielson, San Mateo, CA (US); Anton Kalachev, Burlingame, CA (US); John Wong, Morristown, NJ (US); Behram DaCosta, San Jose, CA (US); Udupi Ramanath Bhat, Mountain View, CA (US); Ludovic Copere, San Jose, CA (US); Masaki Kataoka, Port Washington, NY (US)

(73) Assignees: SONY CORPORATION, Tokyo (JP); SONY CORPORATION OF AMERICA, New York, NY (US)

(*) Notice: Subject to any disclaimer, the term of this patent is extended or adjusted under 35 U.S.C. 154(b) by 0 days.

(21) Appl. No.: 15/236,449

(22) Filed: Aug. 14, 2016

(65) Prior Publication Data
US 2017/0010672 A1 Jan. 12, 2017

Related U.S. Application Data

(63) Continuation of application No. PCT/US2015/016714, filed on Feb. 19, 2015.
(Continued)

(51) Int. Cl.
*G06F 3/01* (2006.01)
*G06F 1/16* (2006.01)
(Continued)

(52) U.S. Cl.
CPC .............. *G06F 3/011* (2013.01); *G06F 1/163* (2013.01); *G06F 1/1637* (2013.01);
(Continued)

(58) Field of Classification Search
CPC ............. G06F 19/3406; G06F 19/3418; G06F 1/1626; G06F 1/163; G06F 1/1637;
(Continued)

(56) References Cited

U.S. PATENT DOCUMENTS

| | | | |
|---|---|---|---|
| 2008/0146892 A1* | 6/2008 | LeBoeuf | A61B 5/11 600/300 |
| 2010/0033303 A1* | 2/2010 | Dugan | A61B 5/0002 340/5.82 |

(Continued)

FOREIGN PATENT DOCUMENTS

| | | |
|---|---|---|
| JP | 09-159482 A | 6/1997 |
| JP | 2007-203913 A | 8/2007 |

(Continued)

OTHER PUBLICATIONS

United States Patent and Trademark Office (USPTO), International Search Report and Written Opinion, PCT International Application No. PCT/US2015/016714, dated Jun. 11, 2015, pp. 1-6, with claims searched, pp. 7-10.

(Continued)

*Primary Examiner* — Tony O Davis
(74) *Attorney, Agent, or Firm* — O'Banion & Ritchey LLP; John P. O'Banion (57) ABSTRACT

A method and apparatus for providing customized haptic feedback for a wearable device with sensors, a processor, memory, haptic outputs and optional communications module. Sensor information is used to provide the context for customizing the haptic feedback.

10 Claims, 3 Drawing Sheets

Related U.S. Application Data (60) Provisional application No. 61/943,837, filed on Feb. 24, 2014.

(51) Int. Cl.

| | | |
|---|---|---|
| *G06F 19/00* | (2018.01) | |
| *H04L 29/06* | (2006.01) | |
| *H04W 12/06* | (2009.01) | |
| *G16H 40/63* | (2018.01) | |
| *G08B 7/00* | (2006.01) | |

(52) U.S. Cl.
CPC ............ *G06F 1/1698* (2013.01); *G06F 1/325* (2013.01); *G06F 1/3206* (2013.01); *G06F 1/3287* (2013.01); *G06F 3/015* (2013.01); *G06F 3/016* (2013.01); *G06F 19/00* (2013.01); *G06F 19/3418* (2013.01); *G16H 40/63* (2018.01); *H04L 63/0861* (2013.01); *H04L 63/0869* (2013.01); *H04W 12/06* (2013.01); *G06F 1/1626* (2013.01); *G08B 7/00* (2013.01); *Y02D 10/171* (2018.01)

(58) Field of Classification Search
CPC ........ G06F 1/1698; G06F 1/3206; G06F 1/32; G06F 1/328; G06F 3/011; G06F 3/015; G06F 3/016; G08B 7/00; H04L 63/0861; H04L 63/0869; H04W 12/06
USPC .......................................... 345/156
See application file for complete search history.

(56) References Cited

U.S. PATENT DOCUMENTS

| | | | | |
|---|---|---|---|---|
| 2011/0260830 A1* | 10/2011 | Weising | ................ | G06F 3/015 340/5.52 |
| 2012/0019373 A1 | 1/2012 | Kruse et al. | | |
| 2012/0188158 A1* | 7/2012 | Tan | ................ | A61B 5/0488 345/156 |
| 2012/0306643 A1* | 12/2012 | Dugan | ................ | A61B 5/02 340/539.12 |
| 2012/0316455 A1 | 12/2012 | Rahman et al. | | |
| 2014/0039900 A1 | 2/2014 | Heubel et al. | | |
| 2014/0164632 A1* | 6/2014 | Kim | ................ | H04L 67/34 709/227 |
| 2014/0205260 A1* | 7/2014 | Lacroix | ................ | H04N 5/765 386/201 |
| 2014/0243710 A1* | 8/2014 | Jeong | ................ | A61B 5/1116 600/594 |
| 2014/0293059 A1* | 10/2014 | Park | ................ | G01S 19/27 348/158 |
| 2015/0070151 A1* | 3/2015 | Cruz-Hernandez | ................ | G11B 27/031 340/407.1 |
| 2015/0120617 A1* | 4/2015 | C. | ................ | G06N 5/027 706/11 |
| 2015/0338919 A1* | 11/2015 | Weber | ................ | G06F 3/016 345/156 |
| 2015/0378434 A1* | 12/2015 | Baskaran | ................ | G06F 3/016 345/156 |
| 2016/0070348 A1* | 3/2016 | Cowley | ................ | G06F 3/016 345/156 |
| 2016/0086457 A1* | 3/2016 | Baron | ................ | G08B 6/00 340/407.1 |
| 2016/0103489 A1* | 4/2016 | Cruz-Hernandez | ..... | G06F 1/163 345/161 |
| 2016/0258758 A1* | 9/2016 | Houston | ................ | G01C 21/20 |
| 2016/0374628 A1* | 12/2016 | Levine | ................ | A61B 5/7455 128/848 |
| 2016/0375307 A1* | 12/2016 | Durham | ................ | A61B 5/112 482/7 |

FOREIGN PATENT DOCUMENTS

| | | |
|---|---|---|
| JP | 2010-155072 A | 7/2010 |
| JP | 2014-001955 A | 1/2014 |
| WO | 2011/056752 A1 | 5/2011 |
| WO | 2013/076615 A1 | 5/2013 |

OTHER PUBLICATIONS

Korean Intellectual Property Office (KIPO), Official Action dated Jul. 10, 2017, related Korean patent application No. 10-2016-7021760, pp. 1-9, English-language translation, pp. 10-16, claims examined, pp. 17-20.

European Patent Office (EPO), Extended European Search Report dated Jul. 28, 2017, related European Patent Application No. EP 15 75 1661, pp. 1-10, with claims searched, pp. 11-14.

Anliker, Urs et al., "AMON: A Wearable Multiparameter Medical Monitoring and Alert System", IEEE Transactions on Information Technology in Biomedicine, vol. 8, No. 4, Dec. 2004, pp. 415-427.

Japanese Patent Office (JPO), Notification of Reasons for Refusal dated Aug. 23, 2017, related Japanese application No. 2016-551292, pp. 11, English-language translation, pp. 12-22, with claims examined, pp. 23-26.

Japanese Patent Office (JPO), Notification of Reasons for Refusal dated Mar. 28, 2018, related Japanese application No. 2016-551292, pp. 1-12, English-language translation, pp. 13-24, with claims examined, pp. 25-29.

Japanese Patent Office (JPO), Notification of Reasons for Refusal dated Nov. 28, 2018, related Japanese application No. 2016-551292, pp. 1-4, English-language translation, pp. 5-8, with claims examined, pp. 9-12.

\* cited by examiner

SMART WEARABLE DEVICES AND METHODS FOR CUSTOMIZED HAPTIC FEEDBACK

CROSS-REFERENCE TO RELATED APPLICATIONS

This application is a 35 U.S.C. § 111(a) continuation of PCT international application number PCT/US2015/016714 filed on Feb. 19, 2015, incorporated herein by reference in its entirety, which claims priority to, and the benefit of, U.S. provisional patent application Ser. No. 61/943,837 filed on Feb. 24, 2014, incorporated herein by reference in its entirety. Priority is claimed to each of the foregoing applications.

The above-referenced PCT international application was published as PCT International Publication No. WO 2015/127143 on Aug. 27, 2015, which publication is incorporated herein by reference in its entirety.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Field of the Technology

This technology pertains generally to smart wearable devices and sensor networks and more particularly to a system of non-wearable and wearable sensor and processing devices with customized haptic feedback.

2. Discussion

Sensors placed on or around an individual can acquire biological or physical data in real time. Both non-invasive and invasive sensors, alone or collectively, can produce data that can be processed to determine the physical or mental status of the user at a particular instant and can demonstrate trends over time. Multiple sensors with the capability of collecting biological or physical data (heart rate, blood oxygen and sugar levels, body temperature and etc.) of a user can be applied with the use of wearable devices.

Other sensors can collect data on the environment including location, altitude, air pollution, pollen count, distance traveled, external temperature etc., can also be considered within the context of the sensor data obtained from a particular user of sensors of a wearable device.

However, there is no way for the sensor data or changes in sensor data from pre-defined levels to be effectively communicated to the user without a display interface. There is currently no customized haptic feedback for a wearable device, customizable by the high level contextual information created by raw sensor information.

Accordingly, there is a need for wearable devices and systems that have customizable haptic feedback based on the characteristics of the sensor data of the sensor apparatus.

BRIEF SUMMARY

This disclosure describes smart wearable devices and methods for providing customizable haptic feedback. The wearable devices have input sensors and output haptic or other devices that are primarily attached to the body of the user when the wearable device is in use. The wearable device can monitor and acquire the wearer's biological or physical data and process the acquired data to determine or detect predetermined health conditions such as heart rate, high stress level, phase of sleep and level of appetite.

Notification of the wearer to the characteristics of the raw or processed sensor data can be made through output devices such as haptic vibration or heating or cooling devices etc. These feedback outputs can be customized by the high level contextual information created by raw sensor information acquired by a wearable device over time.

The user can also associate other devices with the wearable device and can configure the wearable device to activate a certain function of the other devices in response to the determination or detection of predetermined sensor conditions by generating an activation trigger signal and sending the signal to the other devices using the communication interface. The other device which receives the triggering signal may activate certain functions in response to the reception of the triggering signal and may send back an acknowledgement signal to the wearable device. For example, the wearer may be alerted to the occurrence of certain medical conditions sensed by the sensors of the wearable device through a customized haptic, audio or visual indicator.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only.

DETAILED DESCRIPTION

Referring more specifically to the drawings, for illustrative purposes an embodiment of a wearable apparatus and method for producing a customized haptic output based on the processed sensor information and user instructions is described and depicted generally in FIG. 1 through FIG. 4. It will be appreciated that the methods may vary as to the specific steps and sequence and the apparatus may vary as to elements and structure without departing from the basic concepts as disclosed herein. The method steps are merely exemplary of the order in which these steps may occur. The steps may occur in any order that is desired, such that it still performs the goals of the claimed technology.

The present disclosure generally pertains to wearable devices that are capable of, for example, performing an action based on one or more biological or physiological characteristics of the user wearing the device. Using one or more sensors, a processor, and programming code executable on the processor, a wearable device can be configured to sense and process characteristics that include, but are not limited to, a wearer's physical characteristics such as gender, weight, height, body temperature, skin temperature, heart rate, respiration, blood sugar level, blood glucose level, stress/fatigue, galvanic skin response, ingestion (protein), digestion rate, metabolic rate, blood chemistry, sweat, core and skin temperature, vital signs, eye dryness, tooth decay, gum disease, energy storage, calorie burn rate, mental alertness, cardiac rhythm, sleep patterns, caffeine content, vitamin content, hydration, blood oxygen saturation, blood cortisol level, blood pressure, cholesterol, lactic acid level, body fat, protein level, hormone level, muscle mass, pH, etc. Such conditions may also include, but are not limited to, position (e.g., prone, upright), movement, or physical state (e.g., sleeping, exercising), etc.

A wearable device may include one or more output devices that include, but are not limited to, haptic output devices (e.g., offset motors, electroactive polymers, capacitive voltage generators, Peltier temperature elements, contracting materials, Braille coding actuators), telemetry devices, visual devices, audible devices, and other output devices.

A wearable device may include an artificial intelligence so that the device can learn and adapt to an individual wearer. The device may be configured to accurately discriminate between erroneous (accidental, unintended, etc.) and valid sensory inputs, thereby developing accurate conclusions about a wearer's physical state or characteristics (e.g., the device does not interpret a wearer rolling over in their sleep as the wearer exercising). The device may also include one or more cameras or other visual sensors for facial, user, or other image recognition. A wearable device may also be configured to transmit information to and/or retrieve information from a wearer's digital health history.

A wearable device may be configured to output information to a user, to another wearable device, to a non-wearable device, or to a network according to the particular features and function of the device.

A. Generalized System Implementation.

Figure 1:
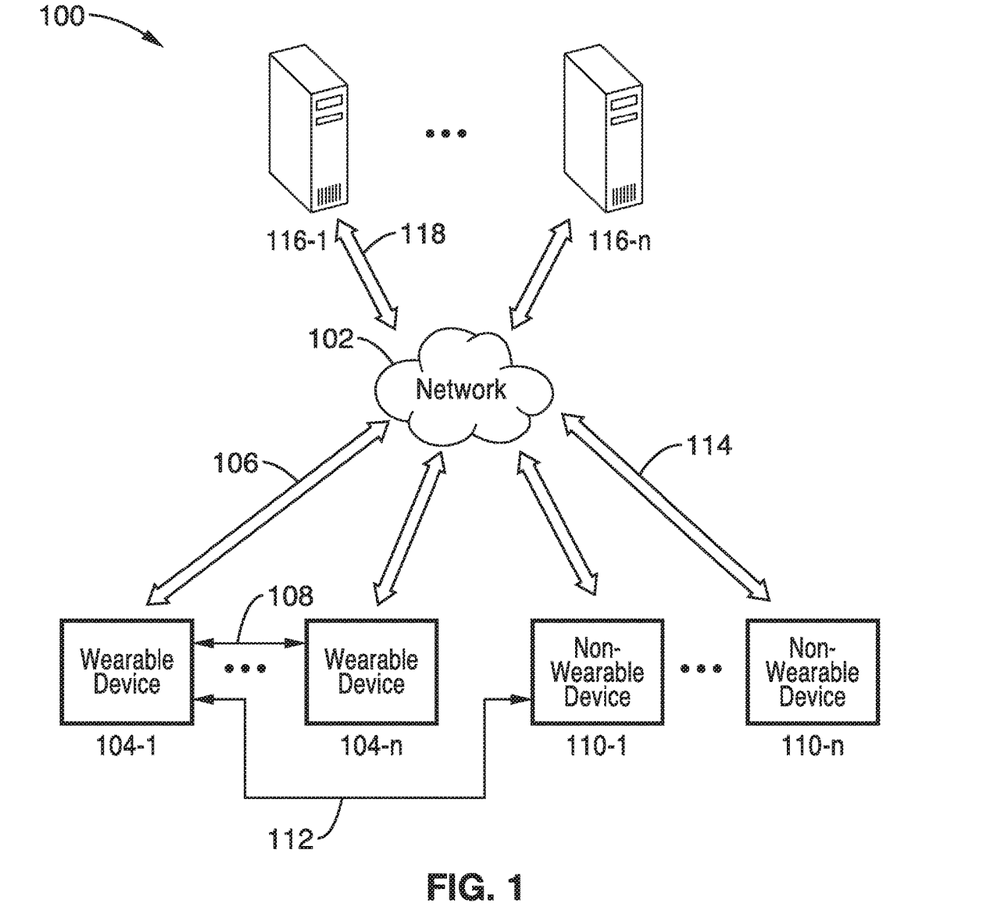
FIG. 1 is a schematic diagram of an embodiment of a smart wearable network described herein.

FIG. 1 illustrates a generalized networked infrastructure (e.g., system) 100 that includes a network 102. The network could, for example, be a local area network or a wide area network such as the Internet. One or more smart wearable devices 104-1 through 104-*n* according to embodiments of the technology described herein may be enabled to communicate with the network 102 through a wired or wireless connection 106. Further, one or more of the smart wearable devices may be enabled to communicate with another smart wearable device through the network 102 or by means of a direct wired or wireless connection 108.

One or more of the smart wearable devices 104-1 through 104-*n* also may be enabled to communicate with one or more non-wearable devices 110-1 through 110-*n*. The non-wearable devices, which are beyond the scope of this disclosure, may be any conventional "smart" device with a processor, associated operating system, and communications interface. Examples of non-wearable devices include smart phones, tablet computers, laptop computers, desktop computers, and set top boxes. Any of the non-wearable devices may be of a type enabled to communicate with an external device through a wired or wireless connection. In that case, one or more of the smart wearable devices may be enabled to communicate with one or more of the non-wearable devices by means of a direct wired or wireless connection 112. Further, one or more of the non-wearable devices may be of a type that is enabled to communicate with the network 102 through a standard wired or wireless connection 114. In that case, one or more of the smart wearable devices may be enabled to communicate with one or more of the non-wearable devices through the network 102.

One or more servers 116-1 through 116-*n* may be provided in a client-server configuration and connected to the network by means of a wired or wireless connection 118. The servers may include standalone servers, cluster servers, networked servers, or servers connected in an array to function like a large computer. In that case, one or more of the smart wearable devices may be enabled to communicate with one or more of the servers.

Figure 2:
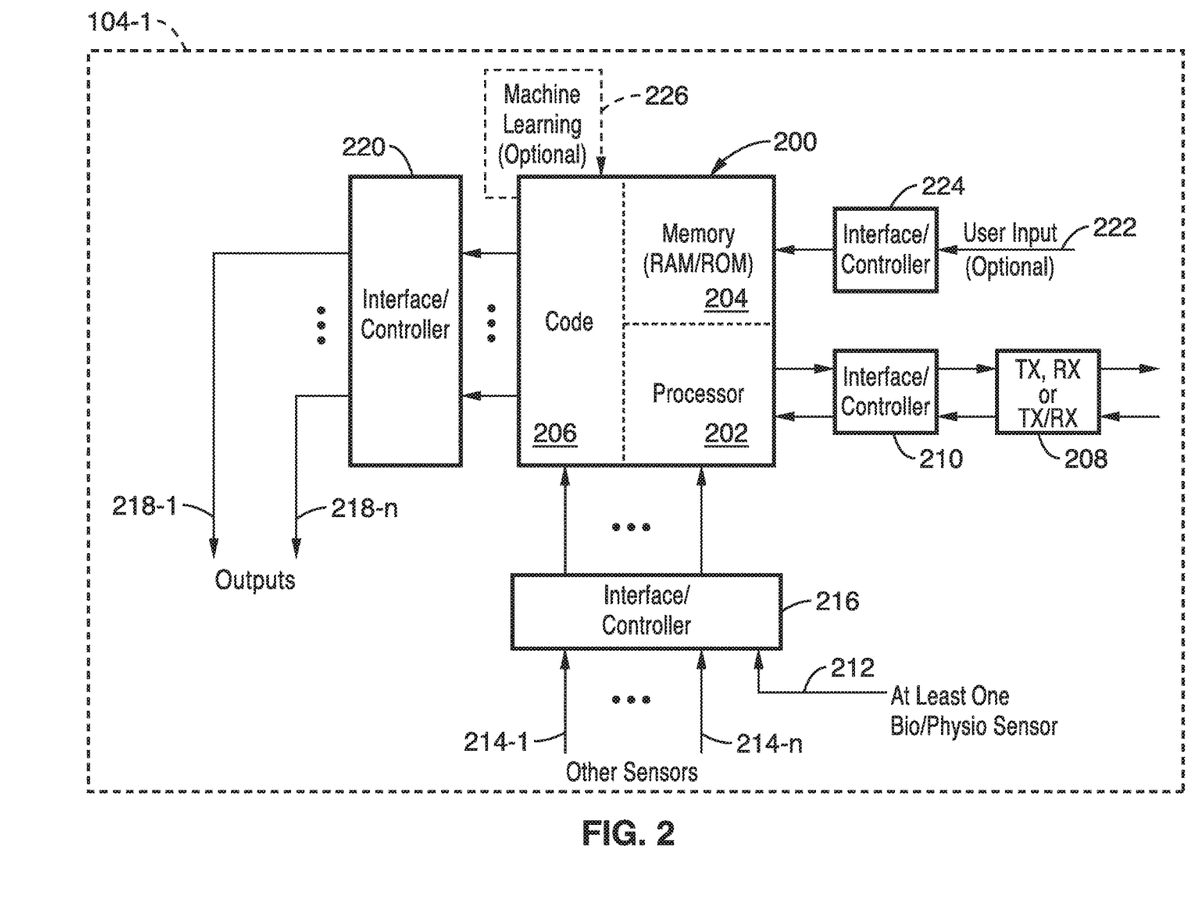
FIG. 2 is a functional block diagram of an embodiment of a smart wearable device described herein.

FIG. 2 illustrates a generalized embodiment of a smart wearable device according to the technology described herein. It will be appreciated that the embodiment shown may be modified or customized to enable performing the functions described herein. In the exemplary embodiment shown, the smart wearable device includes an "engine" 200 having a processor 202, memory 204, and application software code 206. The processor 202 can be any suitable conventional processor. The memory 204 may include any suitable conventional RAM type memory and/or ROM type memory with associated storage space for storing the application programming code 206.

A conventional wired or wireless communications module 208 (e.g., transmitter or receiver or transceiver) may be included as needed for performing one or more of the functions of the smart wearable device described herein. Examples of wireless communication capabilities that can be provided include, but are not limited to, Bluetooth, Wi-Fi, infrared, cellular, and near field communication. One or more conventional interfaces or controllers 210 may also be provided if needed. Examples of interfaces or controllers include, but are not limited to, analog to digital converters, digital to analog converters, buffers, etc.

The device may include at least one input 212 for a biological or physiological sensor for providing input to the device to perform one or more of the functions described herein. Sensor inputs 214-1 through 214-*n* for optional sensors may be included as well. These optional input sensors may include, but are not limited to, accelerometers, temperature sensors, altitude sensors, motion sensors, position sensors, and other sensors to perform the function(s) described herein. One or more conventional interfaces or controllers 216 may be provided if needed for the sensors. Examples of interfaces or controllers include, but are not limited to, analog to digital converters, digital to analog converters, buffers, etc.

Additionally, the device may include one or more outputs 218-1 through 218-*n* to drive one or more output devices (and include those output devices). These output devices may include, but are not limited to, haptic output devices, telemetry devices, visual devices, audible devices, and other output devices to perform the functions described herein. One or more conventional interfaces or controllers 220 may be provided if needed for the output devices. Examples of interfaces or controllers include, but are not limited to, analog to digital converters, digital to analog converters, buffers, etc.

A user input 222 may be provided according to the functions described herein. The user input may, for example, initiate one or more functions, terminate one or more functions, or intervene in a running process. The user input can be any conventional input device, including but not limited to, manual switches, touch sensors, magnetic sensors, proximity sensors, etc. One or more conventional interfaces or controllers 224 may be provided if needed for the output devices. Examples of interfaces or controllers include, but are not limited to, analog to digital converters, digital to analog converters, buffers, etc.

Depending on the function(s) described herein, the engine 200 may also include a feedback loop 226 for machine learning or other adaptive functions. The feedback loop may also provide for device calibration.

It will be appreciated that a smart wearable device as described herein would necessarily include a housing or carrier for the above-described components. It will further be appreciated that, as used herein, the term "smart wearable device" means a device that would be worn or otherwise associated with the body of a user and be "connected" to the user by means of at least one sensor for sensing one or more biological or physiological conditions of the user.

The particular form of the housing or carrier (i.e., wearable platform) can vary according to choice and suitability for performing the functions described herein. Examples of wearable platforms include, but are not limited to, hand worn devices, finger worn devices, wrist worn devices, head worn devices, arm worn devices, leg worn devices, ankle worn devices, foot worn devices, toe worn devices, watches, eyeglasses, rings, bracelets, necklaces, articles of jewelry, articles of clothing, shoes, hats, contact lenses, gloves, etc.

It will further be appreciated that the input sensors and output devices may be integrated into the wearable platform, or may be external to the wearable platform, as is desired and/or suitable for the function(s) of the smart wearable device.

B. Smart Wearable Device with Customizable Haptic Feedback.

Wearable devices with multiple sensors with the capability of collecting data by acquiring biological or physical data (e.g. heart rate, blood oxygen and sugar levels, body temperature and etc.) of a user of the wearable device can be used to determine the physical or mental status of the user over time. Wearable device sensors can also monitor and collect data on the environment (location, altitude, air pollution, distance traveled, external temperature and etc.) surrounding the wearer.

The preferred wearable device can automatically generate appropriate and timely wearer defined feedback signals which can be used to activate communications and haptic output devices determined by the nature of the processed sensor data without the wearer's intervention. This may be particularly important when the wearer of the wearable device is encountering specific mental or health conditions that make it difficult for the wearer to operate other wearable or non-wearable devices at that time.

Figure 3:
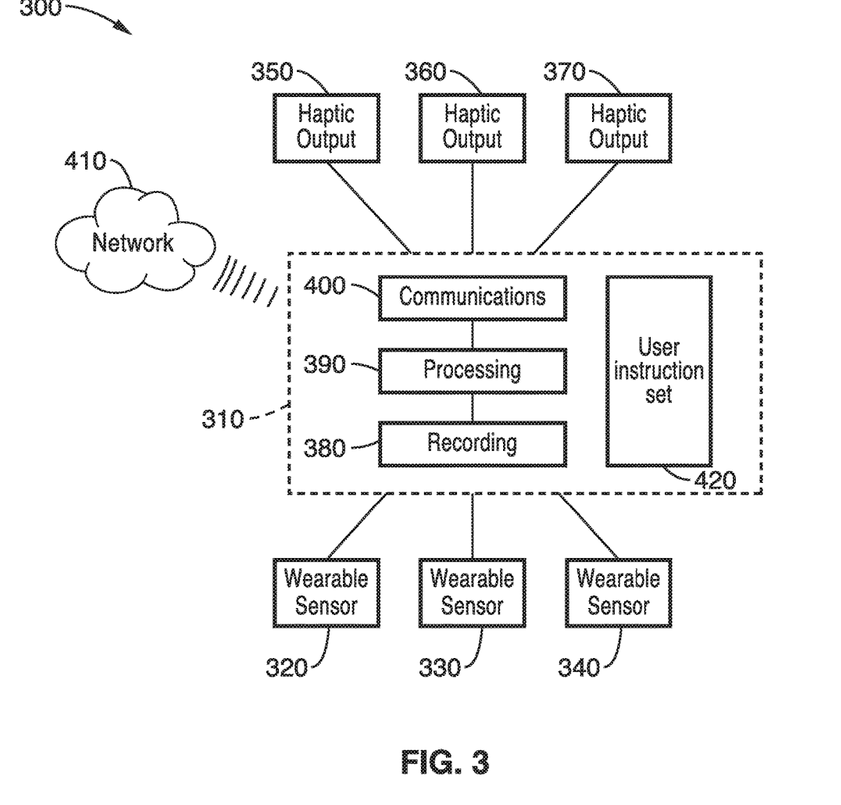
FIG. 3 is a schematic diagram of the processing flow and the data used for one embodiment of the customizable haptic feedback method of the present disclosure.

As seen in the functional diagram of FIG. 3, an embodiment of a wearable device 300 is configured with a processing module 310 with wearable sensors and haptic output devices. The wearable sensors 320, 330 and 340 preferably include at least one sensor providing biological data, such as blood pressure, heart rate, hydration, blood as well as sugar, blood glucose, $SPO_2$, cortisol, skin condition, or lactic acid concentrations. Wearable sensors 320, 330 and 340 may also include sensors such as accelerometers, temperature sensors, altitude sensors, motion sensors, position sensors, and other sensors detecting the physical circumstances of the wearer. In one embodiment, the wearable sensor device has one or more sensors that measure the internal physical conditions of a wearer and one or more sensors that measure the external conditions around the wearer.

The wearable device 300 also has one or more haptic output devices 350, 360 and 370 that can provide different types of sensory feedback to the wearer depending on the raw or processed data obtained from the wearable sensors singly or collectively.

The haptic output devices 350, 360 and 370, are preferably devices that are capable of producing vibrations at different frequencies from a signal from the processing module. Haptic devices can also be heating or cooling devices that can stimulate the heat or cold receptors in the skin of the wearer of the wearable device. In another embodiment, telemetry devices, visual devices, audible devices, and other output devices can be used in addition to perform a variety of notice functions.

The processing module 310 of the wearable device 300 preferably has recording 380, processing 390 and communications 400 functions. The collected raw and processed data from the wearable sensors 320, 330 and 340 can be recorded at block 380 of FIG. 3. The recorded data can be kept within the memory of the processing module 310 and used for evaluating trends and providing a history of sensor activity.

The processing function 390 of the data is used in conjunction with a set of user defined instructions and parameters. In one embodiment, the instructions are in the form of "if-then" directions. For example, if sensor data A" then produce signal "haptic output 1." The instructions can be simple or complex and can account for many different sensor data combinations and potential haptic output responses. In another embodiment, the instruction set 420 may also include non-sensor wearer specific information such as gender, dimensions or limits. The non-sensor information may also include invasive testing information provided from other sources such as blood testing.

In one embodiment, each instruction of the instruction set 420 is assigned a specific haptic output response, which corresponds with a sensor result or group of results. The haptic output or other designated output can alert the wearer of sensor conditions that may require some change in activity, for example. Likewise, the haptic feedback may notify the wearer of a desirable condition and that no change in activity should take place.

The optional communications function 400 can communicate with a remote computation device or cloud network 410 or another non-wearable or wearable device. In one embodiment, the sensor data is acquired from the wearable sensors 320, 330 and 340 and sent to a remote device or network 410 by a wireless transmission for processing and all or part of the instruction set is at that remote location and the haptic output is directed by instructions received by the processing module 310. In this embodiment, the wearer does not need to exert any control over the communications or instructions or evaluate the sensor data.

Figure 4:
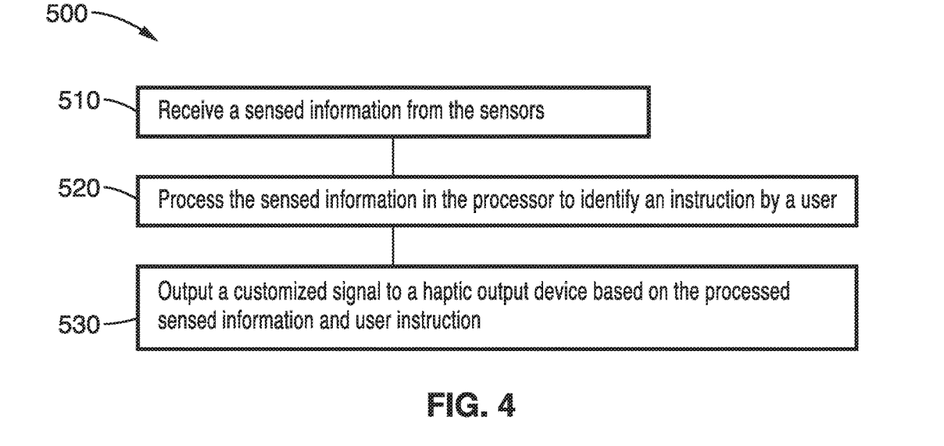
FIG. 4 is a schematic flow diagram of the method for customizable haptic output based on sensor data.

Referring also to FIG. 4, one method 500 for customizing haptic or other output feedback responses of a wearer of a wearable device begins at block 510 with receiving and processing data from one or more sensors. This sensor information may also include prior sensor results from a remote sensor or relevant non-sensor information.

At block 520, the sensor information from block 510 is processed and it is determined whether the information falls within the coverage of an instruction from a defined instruction set for the wearer. If the sensor data falls within an instruction, then a signal is generated for activating at least one haptic output of the wearable device at block 530. In addition, the instruction set may also direct the transmission of the data over the communications link to a remote device.

The designation of the defined instruction set that is used at block 520 can be a haptic output or non-haptic output alone or in combination. The instruction set may also include the transmission of sensor data to a remote computer or to a non-wearable device. In one embodiment, the instruction set includes the specification of a message and a recipient. The message is sent to the specified recipient at the same time as the haptic output is actuated in the wearable device at block 530. In another embodiment, a haptic or non-haptic response is defined to be actuated when the message is sent to the specified recipient. For example, a light or sound could be produced on the wearable device to alert the wearer that a message was sent due to the presence of acquired sensor data matching the designated data.

In another embodiment, the instructions and sensor data can be sent to a remote computer using the communications link. The remote computer may then send programming commands back to the wearable device that can include a specific haptic output.

Accordingly, the customization of the haptic or other response may be made automatically based on the location of the sensor (motion sensor), gender of the wearer (pre-input information), position of limbs (motion sensor with a camera), or sensitivity of skin (camera). The customization may also be made manually based on the strength of the input to the sensor input devices.

It can be seen that the system can be adapted to provide haptic feedback in a variety of contexts. In addition to monitoring the physiological characteristics of a wearer in a stationary environment, the system can also be adapted for use in moving environments such as during travel in a car, bus, train or airplane. For example, when the user is getting into a vehicle, the wearable device can sense that the user is in a vehicle through the use of a Bluetooth signal or a GPS signal.

Once the device recognizes the presence of a user in a vehicle through sensor input, it can adopt a vehicle mode where the feedback signal of the wearable device (e.g., vibration) becomes stronger so that the user can more easily notice the vibration, for example. In one embodiment, the wearable device can be configured as a wrist band type device that has an anti-sleep function. By using a GPS signal together with the motion information of the wrist band type, the wearable device can notice that the user's driving direction have strayed from the center. In that case, the strength of the haptic feedback is set at the maximum level.

In one embodiment, the device incorporates the use of a Bluetooth signal. It is now common in many cars to have a system that transmits and receives commands with a Bluetooth function. The wearable device can change its mode to a car mode when it receives a Bluetooth signal from the car with the starting of the car engine.

Another way to sense the presence of the user in a vehicle is to use a vibration pattern sensed by a wristband type of wearable device. For example, when the user starts the engine of the car and grasps the steering wheel, the wheel vibrates with a particular vibration pattern (e.g., frequency and strength) to the engine and the wearable device senses that vibration. The vibration patterns depend on the speed of the car and the gear. So, the wearable device can determine that the user is driving and the relative speed of the vehicle from the vibrations. In another embodiment, a GPS signal is used by the device. When the user is in the middle of the road travelling at a fast speed, the wearable device can determine that the user is in a moving car based on the changes indicated by the GPS signal.

On the other hand, the wearable device can also determine when the user ends driving and transitions to a stationary environment. For example, the device can determine that the car has been turned off when the Bluetooth signal is turned off. In another embodiment, the device can identify when the travelling of the user ends when there is a change in the observed vibration pattern of the wheel observed when the engine of the vehicle is turned on.

Another embodiment of the device uses the sensor information from several different sources to determine the travelling status of the user. In this example, the wearable device is provided preliminary information about the car such as whether it is an electric car, a hybrid car or a regular gasoline car alone so that the sensed vibration pattern can be correlated and assessed. The travel status of the user can be determined with a combination of a vibration pattern from the wheel, a GSP signal, speed information (accelerometer) or exchanged information between the wearable device and the car via Bluetooth, Wi-Fi or some other type of communications link. Once the wearable device determines that the user is not driving, the mode of the wearable device can change from its car mode (e.g., alerting via car audio and/or a strong vibration) to the regular mode (e.g., alerting by sound and/or a vibration of the regular strength).

In another embodiment, the sensors of the wearable device can be used to alert a drowsy driver, for example, with an alarm initiated by sensor data input to the device. By using motion sensor information, the wearable device obtains and evaluates the sensor data of the user and compares it to a status history for the user to determine whether the user is drowsy. Once the wearable device determines that the user is drowsy, the device strongly vibrates to alert the user. The wearable device can also make a loud sound through a Bluetooth connection and speaker of the car to alert the user. This sound alert can be alone or in combination with a vibration alert.

In another embodiment, certain motions of the user will give characteristic sensor results that can be associated with device commands and used to activate or deactivate functions with a motion. By using motion sensor information, the user can provide instructions to a car or other device via a wristband type wearable device by twisting the wrist in one embodiment. For example, a user with a wristband type of wearable device on his left hand can turn on the music player of the car by twisting the wrist outward quickly, which is an unusual motion of the user in a daily life so that it is easy to distinguish this motion as an instruction from other motions of the user. On the other hand, twisting the wrist inward quickly could turn off the car audio. When the manipulation is successful, the wearable device vibrates in a particular pattern to notify that the user instructed manipulation was successful.

The audible alarms provided by the device can also take different forms that can be selected to provide the most effective alert to the user in a given environment. For example, the wearable device can evaluate the sound environment around the user by using a microphone implemented on the wearable device. If the environment around the user is noisy, the wearable device can switch the nature of the alert from a sound alert to a haptic alert. By switching alerts, the user will be more likely notice the haptic alert than the sound alert in a noisy environment. Alternatively, the volume of an audible alert can be increased or decreased depending on the detection of a loud or quiet environment to provide an appropriate alert.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that "programming" as used herein refers to one or more instructions that can be executed by a processor to perform a function as described herein. The programming can be embodied in software, in firmware, or in a combination of software and firmware. The programming can be stored local to the device in non-transitory media, or can be stored remotely such as on a server, or all or a portion of the programming can be stored locally and remotely. Programming stored remotely can be downloaded (pushed) to the device by user initiation, or automatically based on one or more factors, such as, for example, location, a timing event, detection of an object, detection of a facial expression, detection of location, detection of a change in location, or other factors. It will further be appreciated that as used herein, that the terms processor, central processing unit (CPU), and computer are used synonymously to denote a device capable of executing the programming and communication with input/output interfaces and/or peripheral devices.

From the discussion above it will be appreciated that the technology can be embodied in various ways, including but not limited to the following:

1. A wearable sensor apparatus, comprising: (a) a computer processor with memory; (b) a plurality of sensors operably coupled to the processor; (c) at least one haptic output coupled to the computer processor; (d) programming in a non-transitory computer readable medium and executable on the computer processor for performing steps comprising: (i) designating an output for possible sensor results of each sensor; (ii) acquiring sensor data from at least one sensor worn by a user; (iii) matching the acquired sensor data with possible sensor results; and (iv) initiating the designated output for matching sensor data.

2. The apparatus of any preceding embodiment, wherein the plurality of sensors comprises: at least one biological sensor configured to measure an internal physical condition of a wearer; and at least one non-biological sensor configured to measure an external condition of a wearer.

3. The apparatus of any preceding embodiment, wherein the non-biological sensor is a sensor selected from the group of sensors consisting of an accelerometer, a temperature sensor, an altitude sensor, a motion sensor, and a position sensor.

4. The apparatus of any preceding embodiment, wherein the haptic output is an output device selected from the group of devices consisting of a vibrating device, a heating element, a cooling element, an electroactive polymer, a capacitive voltage generator, and a Braille coding actuator.

5. The apparatus of any preceding embodiment, the wearable apparatus further comprising: at least one non-haptic output device operably coupled to the processor; the output device selected from the group of output devices consisting of telemetry devices, light generating devices and sound generating devices.

6. The apparatus of any preceding embodiment, the wearable apparatus further comprising: (a) a communications link operably coupled to the processor, the link having a transmitter and a receiver; and (b) programming in a non-transitory computer readable medium and executable on the computer processor for performing steps comprising: (i) communicating acquired sensor data to a remote computer; and (ii) executing program commands received from the remote computer.

7. The apparatus of any preceding embodiment, wherein the remote computer comprises a non-wearable device.

8. The apparatus of any preceding embodiment, wherein the communication between the wearable device and the remote computer is a wireless communication system selected from the group of systems consisting of Bluetooth, Wi-Fi, infrared, cellular, and near field communications.

9. The apparatus of any preceding embodiment, wherein the programming further performs steps comprising: designating language of at least one communication and a recipient for at least one possible sensor result; and sending the communication to the recipient over the communications link when the acquired sensor data with possible sensor results match.

10. The apparatus of any preceding embodiment, wherein the communication sent to a recipient over the communications link is a communication selected from the group of communications consisting of a text message, an e-mail message and a recorded message.

11. The apparatus of any preceding embodiment, wherein the programming further performs steps comprising: selecting a non-haptic output for the designated possible sensor result; and actuating the non-haptic output device when the communication is sent to the designated recipient.

12. A computer implemented method for monitoring wearable sensors with customizable feedback, the method comprising: (a) identifying available haptic outputs of a wearable sensor device; (b) designating an output for possible sensor results for each sensor of a wearable sensor device; (c) acquiring sensor data from at least one sensor while being worn by a user; (d) matching the acquired sensor data with possible sensor results; and (e) performing the designated output for matching sensor data; (f) wherein the method is performed by executing programming on at least one computer processor, the programming residing on a non-transitory medium readable by the computer processor.

13. The method of any preceding embodiment, further comprising: communicating acquired sensor data to a remote computer through a communications link; and executing program commands received from the remote computer.

14. The method of any preceding embodiment, further comprising: designating language of at least one communication and a recipient for at least one possible sensor result; and sending the communication to the recipient over the communications link when the acquired sensor data with possible sensor results match.

15. The method of any preceding embodiment, further comprising: selecting an output for the designated possible sensor result; and actuating the output device when the communication is sent to the designated recipient.

Although the description above contains many details, these should not be construed as limiting the scope of the technology but as merely providing illustrations of some of the presently preferred embodiments of this technology. Therefore, it will be appreciated that the scope of the present technology fully encompasses other embodiments which may become obvious to those skilled in the art, and that the scope of the present technology is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present technology, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112 unless the element is expressly recited using the phrase "means for" or "step for".

What is claimed is:

1. A wearable sensor apparatus, comprising:
   (a) a processor;
   (b) a plurality of sensors operably coupled to the processor, said sensors comprising at least one biological sensor configured to measure an internal physical condition of a wearer and at least one non-biological sensor configured to measure an external condition of a wearer;
   (c) at least one haptic output coupled to the processor;
   (d) a communications module operably coupled to the processor, the module having a transmitter and a receiver: and
   (e) programming in a non-transitory computer readable medium and executable on the processor for performing steps comprising:
       (i) designating a haptic output for possible sensor results of each sensor;
       (ii) acquiring sensor data from at least one sensor worn by a user;
       (iii) processing the acquired sensor data with possible sensor results;
       (iv) initiating the designated haptic output for matching sensor data;
       (v) communicating acquired sensor data to a remote computer;
       (vi) executing program commands received from the remote computer;
       (vii) identifying at least one possible sensor result from a sensor;
       (viii) designating a recipient of a communication regarding the sensor result; and
       (ix) sending the communication to the recipient over the communications module when the acquired sensor data and the possible sensor results match.

2. The apparatus of claim 1, wherein said non-biological sensor is a sensor selected from the group of sensors consisting of an accelerometer, a temperature sensor, an altitude sensor, a motion sensor, and a position sensor.

3. The apparatus of claim 1, wherein said haptic output is an output device selected from the group of devices consisting of a vibrating device, a heating element, a cooling element, an electroactive polymer, a capacitive voltage generator, and a Braille coding actuator.

4. The apparatus of claim 1, said wearable apparatus further comprising:
   at least one non-haptic output device operably coupled to the processor;
   the output device selected from the group of output devices consisting of a telemetry device, a light generating device and a sound generating device.

5. The apparatus of claim 1, wherein said remote computer comprises a non-wearable device.

6. The apparatus of claim 1, wherein said communication between said wearable device and said remote computer is a wireless communication system selected from the group of systems consisting of Bluetooth, Wi-Fi, infrared, cellular, and near field communications.

7. The apparatus of claim 1, wherein said communication sent to a recipient over the communications module is a communication selected from the group of communications consisting of a text message, an e-mail message and a recorded message.

8. The apparatus of claim 1, wherein said programming further performs steps comprising:
   selecting a non-haptic output for the designated possible sensor result; and actuating the non-haptic output device when the communication is sent to the designated recipient.

9. A computer implemented method for monitoring wearable sensors with customizable feedback, the method comprising:
- (a) identifying available haptic outputs of a wearable sensor device;
- (b) designating a haptic output for possible sensor results for each sensor of a wearable sensor device;
- (c) acquiring sensor data from at least one biological sensor configured to measure an internal physical condition of the user and at least one non-biological sensor configured to measure an external condition of the user;
- (d) matching the acquired sensor data with possible sensor results; and
- (e) performing the designated haptic output for matching sensor data;
- (f) communicating acquired sensor data to a remote computer through a communications module;
- (g) executing program commands received from the remote computer;
- (h) designating language of at least one communication and a recipient for at least one possible sensor result; and
- (i) sending the communication to the recipient over the communications link when the acquired sensor data with possible sensor results match;
- (j) wherein said method is performed by executing programming on at least one processor, said programming residing on a non-transitory medium readable by the processor.

10. A method as recited in claim 9, further comprising:
selecting an output for the designated possible sensor result; and
actuating the output device when the communication is sent to the designated recipient.

* * * * *